United States Patent [19]

Kajitani et al.

[11] Patent Number: 5,447,944
[45] Date of Patent: Sep. 5, 1995

[54] CARBAMOYL-2-PYRROLIDINONE COMPOUNDS

[75] Inventors: Makoto Kajitani, Saitama; Etsuo Hasegawa; Akihiro Kawaguchi, both of Honjo; Junji Yamamoto; Katsuo Toide, both of Tokushima; Takaji Honna, Tokyo; Mitsugi Yasumoto, Honjo; Nobuo Kasahara, Tokushima, all of Japan

[73] Assignee: Taiho Pharmaceutical Company, Limited, Tokyo, Japan

[21] Appl. No.: 216,244

[22] Filed: Mar. 22, 1994

Related U.S. Application Data

[60] Continuation of Ser. No. 976,843, Nov. 16, 1992, abandoned, which is a division of Ser. No. 449,923, Dec. 13, 1989, Pat. No. 5,229,402.

[30] Foreign Application Priority Data

Apr. 15, 1988 [JP] Japan .................................. 63-93967
Apr. 15, 1988 [JP] Japan .................................. 63-93968

[51] Int. Cl.$^6$ ................... A61K 31/425; A61K 31/40; A61K 31/44; C07D 207/12
[52] U.S. Cl. .................................. 514/371; 514/343; 514/423; 546/281; 548/195; 548/538
[58] Field of Search ................. 548/195, 538; 546/281; 514/371, 423, 343

[56] References Cited

U.S. PATENT DOCUMENTS 5,229,402  7/1993  Kajitani et al. ................. 548/538 X

FOREIGN PATENT DOCUMENTS 2018820   6/1970   France .
52-25026  2/1977   Japan .
54-66265  5/1979   Japan .
53-153763 11/1980  Japan .

OTHER PUBLICATIONS

Patent Journal (Including Trademark & Designs), May 1970, p. 146, abstract of 69/6693.

*Primary Examiner*—Joseph Paul Brust
*Attorney, Agent, or Firm*—Nikaido, Marmelstein, Murray & Oram

[57] ABSTRACT

The present invention provides carbamoyl-2-pyrrolidinone compounds useful as medicaments for improving cerebral functions and activating cerebral metabolism or protecting against anoxic brain damage.

13 Claims, No Drawings

CARBAMOYL-2-PYRROLIDINONE COMPOUNDS

This application is a continuation of application Ser. No. 07/976,843 filed Nov. 16, 1992, now abandoned, which is a divisional of Ser. No. 07/449,923, filed Dec. 13, 1989, now U.S. Pat. No. 5,229,402, issued Jul. 20, 1993.

TECHNICAL FIELD

The present invention relates to novel carbamoyl-2-pyrrolidinone compounds, and cerebral function improving compositions and cerebral metabolism activating or anoxic brain damage protecting compositions comprising the compound.

BACKGROUND ART

Carbamoyl-2-pyrrolidinone compounds are disclosed as herbicides in French Patent No. 2018820, as horticultural fungicides in JP-A-52-25026, or as agents for improving the quality of citrus fruits in JP-A-54-66265, 55-81857 and 55-153763, whereas nothing has been described about their use in compositions for improving cerebral functions and in compositions for activating cerebral metabolism or protecting anoxic brain damage as disclosed in the present invention.

Furthermore, even if some of the compounds defined in the claims appended hereto should be included in the group of compounds represented by the broad general formulae in the above prior-art literature, they have been deleted during the examination procedures, or are not identified in any way in the detailed description of the specifications. Thus, they have not been disclosed in any way specifically and are novel compounds. The other compounds of the present invention are novel compounds which have not been described in any literature.

With an increase in the population of advanced ages in recent years, patients with senile dementia are expected to increase in number, posing a serious problem medically and socially. Although various antidementia drugs have been investigated and developed in view of the situation, no compounds have been provided with satisfactory efficacy up to date. It has been strongly desired to develop medicaments for treating the disease.

An object of the present invention is to provide novel carbamoyl-2-pyrrolidinone compounds which are very useful as medicaments for treating senile dementia, i.e., as cerebral function improving agents and cerebral metabolism activators or anoxic brain damage protectives.

DISCLOSURE OF THE INVENTION

The present invention provides carbamoyl-2-pyrrolidinone compounds represented by the formula

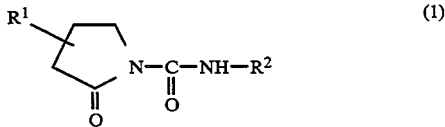

(1)

wherein $R^1$ is a hydrogen atom, hydroxyl or lower alkyl substituted or unsubstituted with hydroxyl, and $R^2$ is phenyl, tetrahydronaphthyl, pyridyl or thiazolyl having or not having methoxy or lower alkylamino as a substituent, provided that when $R^1$ is a hydrogen atom or unsubstituted lower alkyl, $R^2$ is not unsubstituted phenyl.

Exemplary of lower alkyl groups represented by $R^1$ herein and unsubstituted with hydroxyl are straight-chain or branched-chain alkyl groups having 1 to 5 carbon atoms, such as methyl, ethyl, n-propyl, isopropyl, n-butyl, isobutyl, sec-butyl, tert-butyl, n-pentyl and isopentyl. Examples of lower alkyl groups similarly represented and substituted with hydroxyl are lower alkyl groups containing 1 or 2 hydroxyl groups, such as hydroxymethyl, 1-hydroxyethyl, 2-hydroxyethyl, 1-hydroxy-1-methylethyl, 2-hydroxy-1-methylethyl, 1,2-dihydroxyethyl, 1,2-dihydroxy-1-methylethyl, 1-hydroxypropyl, 2-hydroxypropyl, 3-hydroxypropyl and 1,2-dihydroxypropyl.

Examples of lower alkylamino groups included in groups represented by $R^2$ are mono- or di-alkylamino groups atoms, such as methylamino, dimethylamino, ethylamino, diethylamino, propylamino, and dipropylamino.

When $R^2$ in the formula (1) represents a substituted phenyl group, the group preferably has 1 to 3 substituents.

Among the compounds of the formula (1), preferable are those wherein $R^1$ is a hydrogen atom, hydroxyl, methyl or hydroxymethyl, and $R^2$ is phenyl, tetrahydronaphthyl, pyridyl or thiazolyl having 1 to 3 methoxy groups or dimethylamino. More preferable are compounds of the formula (1) wherein $R^1$ is a hydrogen atom or hydroxyl, and $R^2$ is phenyl or tetrahydronaphthyl having methoxy.

We have further found that carbamoyl-2-pyrrolidinone compounds represented by the formula (2)

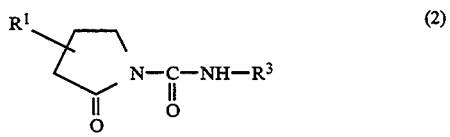

(2)

wherein $R^1$ is a hydrogen atom, hydroxyl or lower alkyl substituted or unsubstituted with hydroxyl, and $R^3$ is phenyl, tetrahydronaphthyl, pyridyl or thiazolyl having or not having lower alkoxy, lower alkylamino, a halogen atom or halogenomethyl as a substituent have an excellent cerebral function improving effect, cerebral metabolism activating or anoxic brain damage protecting effect and effect against senile dementia.

Accordingly, the present invention provides a cerebral function improving composition and a cerebral metabolism activating or anoxic brain damage protecting composition each comprising an effective amount of a compound of the formula (2) and a pharmacologically acceptable carrier.

The present invention further provides a method of improving cerebral functions and activating cerebral metabolism or protecting anoxic brain damage characterized by administering an effective amount of a compound of the formula (2).

Examples of lower alkoxy groups included in groups represented by $R^3$ in the formula (2) are straight-chain or branched-chain alkoxy groups having 1 to 5 carbon atoms, such as methoxy, ethoxy, n-propoxy, isopropoxy, n-butoxy, isobutoxy, sec-butoxy, tert-butoxy, n-pentyloxy and isopentyloxy. Examples of halogen atoms are fluorine, chlorine, bromine, iodine and the like. Examples of halogenomethyl groups are trifluoromethyl, chloromethyl and the like. Examples of lower alkylamino groups are those exemplified for $R^2$.

When $R^3$ in the formula (2) represents a substituted phenyl group, the group preferably has 1 to 3 substituents.

The compounds of the formula (2) have pharmacological activities to ameliorate:

(1) cerebral damage in anoxia, and
(2) amnesia induced by scopolamine in passive condition avoidance response.

These pharmacological properties are useful for activating injured nervous cells and ameliorate memory and learning disturbances.

Accordingly, the compounds of the present invention are usable not only as medicaments for use in treating deterioration of intelligence or neurasthenia, ammnesia, senile dementia or intellectual fatigue, cerebrovascular dementia, aftereffects of encephalopathy and Alzheimer's disease but also as medicaments for improving other cerebral functions or for activating cerebral metabolism or protecting anoxic brain damage.

The carbamoyl-2-pyrrolidinone compound of the present invention can be prepared by one of the following processes.

Process A

This process is characterized by reacting a 2-pyrrolidinone compound represented by the formula (3) with N,N'-carbonyldiimidazole represented by the formula (4) to obtain a 1-imidazolylcarbonyl-2-pyrrolidinone compound represented by the formula (5), and subsequently reacting the compound (5) with an amine represented by the formula (6) to obtain a 1-carbamoyl-2-pyrrolidinone compound (1). The process is represented by the reaction scheme below.

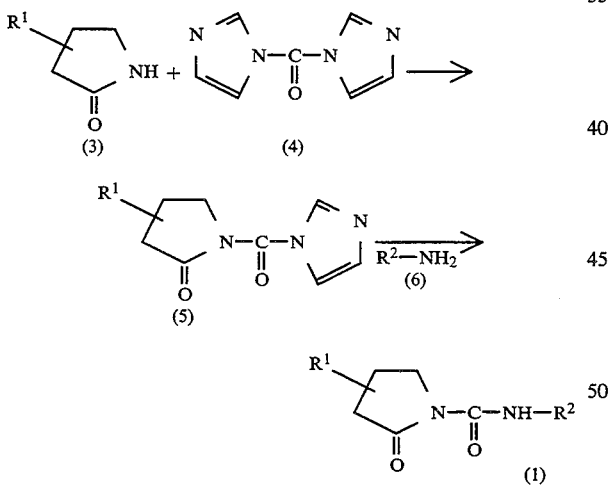

In the above reaction scheme, the compound (3) is reacted with the compound (4) usually in a solvent, which is not limited specifically insofar as it does not participate in the reaction. Examples of solvents generally useful are ethers such as ethyl ether, dioxane and tetrahydrofuran, hydrocarbon halides such as methylene chloride, chloroform, dichloroethane and carbon tetrachloride, aromatic hydrocarbons such as benzene, toluene and xylene, aprotic polar solvents such as dimethylformamide, dimethyl sulfoxide and hexamethylphosphoric acid triamide, etc. Although the compound (3) and the compound (4) may be used in a suitably determined ratio, it is generally advantageous to use 1 to 2 moles, preferably 1 mole, of the compound (4) per mole of the compound (3). While the reaction temperature may also be determined suitably, the reaction proceeds advantageously when conducted at room temperature to 150° C., preferably approximately at the reflux temperature of the solvent. The compound (5) thus obtained can be reacted, as isolated or without being isolated, with the amine (6). This reaction is conducted usually in a solvent, which is not limited specifically insofar as it does not participate with the reaction. The solvents exemplified for use in the reaction between the compound (3) and the compound (4) are generally useful. It is advantageous to use the compound (5) and the amine (6) in the ratio of 1 to 2 moles, preferably 1 mole, of the amine (6) per mole of the compound (5). Although the reaction temperature may be determined suitably, the reaction proceeds advantageously when conducted generally at room temperature to 150° C., preferably approximately at the reflux temperature of the solvent.

In the case of the 2-pyrrolidinone compounds of the formula (3) wherein the substituent for the group $R^1$ is hydroxyl, the compound can be protected with a known protective group which is usually used. Examples of such protective groups are those which will not react with N,N'-carbonyldiimidazole represented by the formula (4), such as tetrahydrofuranyl, tetrahydropyranyl, trimethylsilyl, tert-butyldimethylsilyl and benzyl. These protective groups can be removed easily by usual known means, for example, by an inorganic acid such as hydrochloric acid, sulfuric acid or nitric acid, organic acid such as p-toluenesulfonic acid, acetic acid, oxalic acid or maleic acid, or catalytic reduction.

Process B

This process is characterized by reacting a 2-pyrrolidinone compound represented by the formula (3) with an isocyanate compound (7) to obtain a 1-carbamoyl-2-pyrrolidinone compound and is represented by the following reaction scheme.

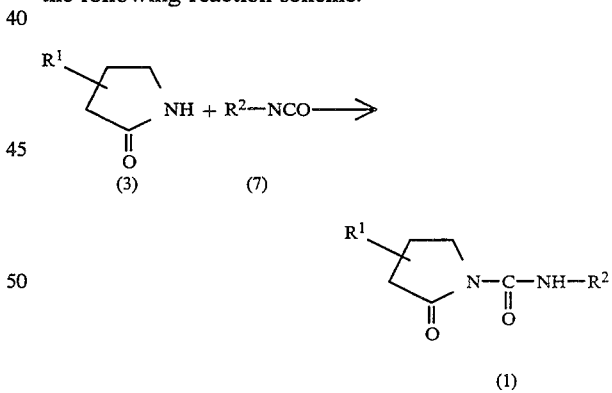

With reference to the above scheme, the compound (3) is reacted with the compound (7) usually in a solvent, which is not limited specifically insofar as it does not participate in the reaction. Examples of solvents generally useful are ethers such as ethyl ether, dioxane and tetrahydrofuran, hydrocarbon halides such as methylene chloride, chloroform, dichloroethane and carbon tetrachloride, aromatic hydrocarbons such as benzene, toluene and xylene, aprotic polar solvents such as dimethylformamide, dimethyl sulfoxide and hexamethylphosphoric acid triamide, etc. A suitable condensation assisting agent is used for the reaction when required. Examples of such agents are sodium hydride, lithium hydride, potassium hydride, potassium tert-butoxide, trialkylamines, pyridine and like basic compounds, and anhydrous aluminum chloride, anhydrous stannic chloride, titanium tetrachloride and like Lewis acids. Although the proportions of the compound (3), the compound (7) and the condensation assisting agent are suitably determined, it is generally advantageous to use 1 to 3 moles, preferably 1 mole, of each of the compound (7) and the condensation assisting agent per mole of the compound (3). While the reaction temperature is determined also suitably, the reaction proceeds advantageously when carried out approximately at $-20°$ C. to the reflux temperature of the solvent.

The process A or B produces the 1-carbamoyl-2-pyrrolidinone compound (1) of the invention, which can be readily isolated by a usual separating method, such as recrystallization, column chromatography or the like.

When the 1-carbamoyl-2-pyrrolidinone compound of the present invention is to be administered for the purpose of treating deterioration of intelligence or neurasthenia, amnesia, senile dementia or intellectual fatigue, and Alzheimer's disease, the compound is administered in the form of a pharmacological preparation such as oral preparation, injection, suppository or the like. These preparations can be produced by conventional methods already known to those skilled in the art.

Solid preparations for oral administration can be produced in a usual manner by adding to the present compound an excipient, and when required, a binder, disintegrator, lubricant, coloring agent, corrigent, flavor and the like, and making the mixture into tablets, granules, powders or an encapsulated preparation. Such additives are those generally used in the art. Examples of useful excipients are lactose, sucrose, sodium chloride, glucose, starch, calcium carbonate, kaolin, microcrystalline cellulose, silicic acid and the like. Examples of useful binders are water, ethanol, propanol, syrup, glucose solution, starch solution, gelatin solution, carboxymethyl cellulose, hydroxypropyl cellulose, hydroxypropyl starch, methyl cellulose, ethyl cellulose, shellac, calcium phosphate, polyvinylpyrrolidone and the like. Examples of useful disintegrators are dried starch, sodium alginate, agar powder, sodium hydrogencarbonate, calcium carbonate, sodium laurylsulfate, stearic acid monoglyceride, starch, lactose and the like. Examples of useful lubricants are purified talc, stearic acid salts, borax, polyethylene glycol and the like. Examples of useful corrigents are sucrose, bitter orange peel, citric acid, tartaric acid and the like.

Liquid preparations for oral administration can be produced by adding a corrigent, buffer, stabilizer, flavor and the like to the present compound, and making the mixture into a liquid oral preparation, syrup, elixir or the like. Examples of useful corrigents are those exemplified above. Exemplary of useful buffers are sodium citrate and the like. Examples of useful stabilizers are tragacanth, gum arabic, gelatin and the like.

Injections can be produced in a usual manner by adding a pH adjusting agent, buffer, stabilizer, isotonic agent, local anesthetic and the like to the present compound, and formulating the mixture into a preparation for subcutaneous, intramuscular or intravenous injection. Examples of useful pH adjusting agents and buffers are sodium citrate, sodium acetate, sodium phosphate and the like. Examples of useful stabilizers are sodium pyrosulfite, EDTA, thioglycolic acid, thiolactic acid and the like. Examples of useful local anesthetics are procaine hydrochloride, lidocaine hydrochloride and the like.

Suppositories can be prepared by adding to the present compound a pharmaceutical carrier known in the art, such as polyethylene glycol, lanolin, cacao fat, fatty acid triglyceride or the like, along with Tween (registered trademark) or like surfactant and the like when desired, and treating the mixture in the usual manner.

Although the amount of the present compound to be contained in the unit form of each preparation varies with the symptoms of the patient, the type of preparation, etc., the amount is generally preferably about 1 to about 300 mg for oral administration, about 1 to about 50 mg for injection or about 1 to 200 mg for suppositories, per unit of the preparation. The dosage of the compound to be given in the form of such a preparation can not be determined specifically but varies with the symptoms, weight, age, sex, etc. of the patient. However, it is given usually at a does of about 0.5 to about 1000 mg, preferably 1 to 500 mg, per day for adults, preferably once or in up to four divided doses. Best mode of carrying out the invention The present invention will be described below in greater detail with reference to examples wherein 1-carbamoyl-2-pyrrolidinone compounds of the formula (1) were prepared, and to the tests conducted to determine the antiamnesia activity and antianoxia activity of compounds (2) and the acute toxicity test thereof.

1-Carbamoyl-2-pyrrolidinone compounds represented by the formula (1) were prepared by the process A or B as described in the following preparation examples. Table 1 shows the properties of the compounds thus prepared and also those of the compounds obtained in the same manner as in these preparation examples.

Compounds 1, 3 and 13 are known compounds disclosed in French Patent No. 2018820 and were prepared by the process A.

EXAMPLE 1

Preparation of 1-(4-methoxyphenylcarbamoyl)-2-pyrrolidinone (process A, Compound 2)

N,N'-Carbonyldiimidazole (3.85 g) and 2 g of 2-pyrrolidinone were added to 20 ml of tetrahydrofuran, and the mixture was refluxed with heating for 8 hours. Next, 2.9 g of 4-methoxyaniline was added to the reaction mixture, and the mixture was further refluxed with heating for 8 hours. The solvent was then distilled off, and the resulting residue was subjected to silica gel column chromatography to obtain a chloroform eluate and crystals from, the eluate. The crystal were recrystallized from methanol, giving 4.7 g of 1-(4-methoxyphenylcarbamoyl)-2-pyrrolidinone (yield 85%) having a melting point of 113° to 114° C.

EXAMPLE 2

Compounds 5 to 10 and 15 were prepared in the same manner as in Example 1.

EXAMPLE 3

Preparation of 1-phenylcarbamoyl-4-hydroxy-2-pyrrolidinone (process A, Compound 11)

A 8.14 g quantity of 4-trimethylsilyloxy-2-pyrrolidinone [Farmaco Edizione Scientifica, 36, 845–855 (1981)] was dissolved in 100 ml of tetrahydrofuran, 7.62 g of N,N'-carbonyldiimidazole was added to the solution, and the mixture was refluxed for 20 hours. With addition of 4.38 g of aniline, the mixture was further refluxed for 7 hours, then cooled and stirred at room temperature for 0.5 hour with addition of 150 ml of 1N hydrochloric acid. The solvent was distilled off in a vacuum, the residue was subjected to silica gel column chromatography to obtain crystals from an eluate of chloroform/methanol=30/1. The crystals were recrystallized from acetone-hexane, giving 7.44 g of 1-phenylcarbamoyl-4-hydroxy-2-pyrrolidinone (yield 72%) having a melting point of 104° to 104.5° C.

EXAMPLE 4

Compound 12 was prepared in the same manner as in Example 3.

EXAMPLE 5

Preparation of 5-hydroxymethyl-1-phenylcarbamoyl-2-pyrrolidinone (process A, Compound 16)

A 5 g quantity of 5-hydroxymethyl-2-pyrrolidinone [Journal of Organic Chemistry, 45, 816 (1980)] was dissolved in 10 ml of dihydropyran, 0.1 ml of concentrated hydrochloric acid was added to the solution, and the mixture was stirred at room temperature for 4 hours. Excessive dihydropyran was distilled off in a vacuum, and the residue was subjected to silica gel column chromatography to obtain an eluate of benzene/ethyl acetate=9/1, which gave 7.9 g of 5-(2-tetrahydropyranoxy)methyl-2-pyrrolidinone (yield 90%).

The 5-(2-tetrahydropyranoxy)methyl-2-pyrrolidinone (5 g), 4.1 g of N,N'-carbonyldiimidazole and 2.33 g of aniline were reacted in the same manner as in Example 1 to obtain 7.96 g of 1-phenylcarbamoyl-5-(2-tetrahydropyranoxy)methyl-2-pyrrolidinone.

The 1-phenylcarbamoyl-5-(2-tetrahydropyranoxy)-methyl-2-pyrrolidinone (7.96 g) was dissolved in 20 ml of methanol, and the solution was stirred at room temperature for 3 hours with addition of 8.6 g of p-toluenesulfonic acid. The solvent was distilled off in a vacuum, 100 ml of water was added to the residue, and the mixture was subjected to extraction with chloroform. The extract was dried over magnesium sulfate and distilled in a vacuum to remove the solvent. The residue was subjected to silica gel column chromatography to obtain an eluate of chloroform/methanol=9/1, which gave 4.86 g of 5-hydroxymethyl-1-phenylcarbamoyl-2-pyrrolidinone (yield 83%) having a melting point of 99° to 101° C.

EXAMPLE 6

Preparation of 3-methyl-1-(4-methoxyphenylcarbamoyl)-2-pyrrolidinone (process B, Compound 14)

While 2 g of sodium hydride (60% oily) was being stirred in 50 ml of tetrahydrofuran, 5 g of 3-methyl-2-pyrrolidinone was added to the mixture, and the resulting mixture was stirred at room temperature for 1 hour. The reaction mixture was cooled to not higher than 0° C., and 7.5 g of 4-methoxyphenyl isocyanate was added dropwise to the mixture, followed by stirring at the same temperature for 5 hours. Acetic acid was then added to the reaction mixture for neutralization, water was thereafter added to the mixture, and the solvent was distilled off in a vacuum. Water was added to the residue, and the precipitate was filtered off, giving 8.2 g of 3-methyl-1-(4-methoxyphenylcarbamoyl)-2-pyrrolidinone (yield 66%) having a melting point of 71° to 72° C.

EXAMPLE 7

Compound 4 was prepared in the same manner as in Example 6.

EXAMPLE 8

| | |
|---|---|
| Compound 5 | 200 mg |
| Lactose | 500 mg |
| Corn starch | 280 mg |
| Hydroxypropyl cellulose | 20 mg |

The above ingredients in the proportions given were made into a granular preparation by the usual method in an amount of 1000 mg per wrapper.

EXAMPLE 9

| | |
|---|---|
| Compound 1 | 100 mg |
| Lactose | 85 mg |
| Microcrystalline cellulose | 50 mg |
| Hydroxypropyl starch | 30 mg |
| Talc | 4 mg |
| Magnesium stearate | 1 mg |

By the usual method, the above ingredients in the proportions given were made into tablets each weighing 270 mg.

EXAMPLE 10

| | |
|---|---|
| Compound 11 | 100 mg |
| Lactose | 50 mg |
| Potato starch | 50 mg |
| Microcrystalline cellulose | 109 mg |
| Magnesium stearate | 1 mg |

By the usual method, the above ingredients in the proportions given were made into an encapsulated preparation in an amount of 310 mg in each capsule.

EXAMPLE 11

| | |
|---|---|
| Compound 3 | 250 mg |
| Fatty acid triglyceride | 750 mg |

By the usual method, the above ingredients in the proportions given were made into suppositories each weighing 1000 mg.

EXAMPLE 12

| | |
|---|---|
| Compound 12 | 5 mg |
| Sodium chloride | 18 mg |

The above ingredients in the proportions given were made into an injection by the usual method.

Test Example 1

Reversal activity of amnesia

1. Animals

Groups of 6 to 16 rats (Wistar, males, weighing 170 to 240 g) were used for the experiment.

2. Drug

Scopolamine was used as dissolved in physiological saline, and the test compound as dissolved or suspended in 0.5% solution of sodium carboxymethyl cellulose.

Scopolamine was used as dissolved in physiological saline, and the test compound as dissolved or suspended in 0.5% solution of sodium carboxymethyl cellulose.

Scopolamine was subcutaneously given at a dose of 0.5 mg/kg 30 minutes before aquisition trials. The test compound was orally given immediately after the aquisition trials.

3. Method

A step-through passive avoidance apparatus was used with reference to Psychopharmacology, 78, 104~111 (1982) and Japan Journal of Pharmacology, 37, 300~302 (1985). The apparatus consisted of a dark compartment (25×12×30 cm) having a grid serving as a floor, and a light compartment (25×12×12 cm) illuminated with 20-W daylight fluorescent lamp from above and separated from the dark compartment by a guillotine door. The rat was subjected to habituation trials about 1 hour before aquisition trials. The habituation was accomplished by placing the rat into the light compartment, opening the door 5 seconds thereafter, closing the door when the four legs completely entered the dark compartment, leaving the rat in the dark compartment for 10 seconds and thereafter taking out the rat. The acquisition trial was accomplished in the same manner as the habituation 1 hour thereafter except that simultaneously when the door was closed upon the movement of the rat into the dark compartment, an unescapable foot shock of 4.5 mA was given to the rat by the floor grit for 1 second.

A retention test was conducted 24 hours after the aquisition trials to measure the step-through latency during which the rat placed into the light compartment remained therein before moving into the dark compartment, i.e., the duration of a passive avoidance reaction.

For a rat exhibiting the avoidance reaction for more than a maximum period of time measured (300 seconds), 300 seconds was recorded. Table 2 shows the result in terms of an increase ratio (%) of the step-through latency based on that of the control group.

Test Example 2

Antianoxic activity test (effect on the survival time under low-oxygen load at atmospheric pressure)

Groups of 10 mice (ddY, five-week-old males) were used for the experiment with reference to Japan Journal of Pharmacology, 81, 421~429 (1983), same, 86, 323~328 (1985) and same, 89, 355~363 (1987). The test compound was orally given to the mouse as dissolved or suspended in 0.5% solution of sodium carboxymethyl cellulose, the mouse was placed into a transparent plastics container (13×13×16 cm) having a vent, and a gas mixture of 96% nitrogen and 4% oxygen was passed through the container at a rate of 5 liters/min. The mouse was observed with the start of passage of the gas until respiratory failure to measure the survival time (seconds). Table 3 shows the result in terms of an increase ratio (%) of the survival time based on that of the control group.

Test Example 3

Acute toxicity test

Mice (ddY, five-week-old males) were used in groups of 4 to 5 mice each. The test compound was dissolved or suspended in 0.5% solution of sodium carboxymethyl cellulose and administered orally. The mice were observed for 3 days to measure the number of deaths. Many of the test compounds produced symptoms of sedation or muscular relaxation for 30 minutes to 6 hours, followed by gradual recovery. The original state was restored two days later. Table 3 shows the result.

TABLE 1

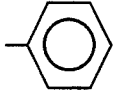

| Compd. No. | $R^1$ | $R^2$ | Process | m.p. (°C.) | Formula | Elementary analysis Calcd (Found) C | H | N |
|---|---|---|---|---|---|---|---|---|
| 1 | H | 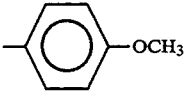 | A | 91~92.5 | $C_{11}H_{12}N_2O_2$ | 64.69 (64.91) | 5.92 (5.89) | 13.72 (13.87) |
| 2 | H | 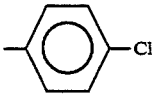—OCH$_3$ | A | 113~114 | $C_{12}H_{14}N_2O_3$ | 61.53 (61.76) | 6.02 (6.08) | 11.96 (11.79) |
| 3 | H | 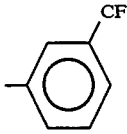—Cl | A | 139~141 | $C_{11}H_{11}N_2O_2Cl$ | 55.36 (55.53) | 4.65 (4.86) | 11.74 (11.64) |
| 4 | H | CF$_3$ (phenyl) | B | 107.5~108.5 | $C_{12}H_{11}N_2O_2F_3$ | 53.03 (52.95) | 4.09 (4.07) | 10.25 (10.29) |

TABLE 1-continued
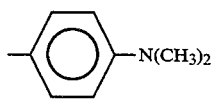
| Compd. No. | R¹ | R² | Process | m.p. (°C.) | Formula | Elementary analysis Calcd (Found) | | |
|---|---|---|---|---|---|---|---|---|
| | | | | | | C | H | N |
| 5 | H | 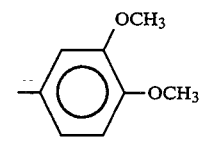 —N(CH₃)₂ | A | 199~201 | $C_{13}H_{17}N_3O_2 \cdot HCl$ | 55.03 (54.79) | 6.39 (6.50) | 14.81 (14.76) |
| 6 | H | 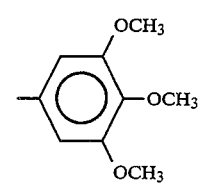 OCH₃, OCH₃ | A | 148~150 | $C_{13}H_{16}N_2O_4$ | 59.08 (59.08) | 6.10 (6.15) | 10.61 (10.61) |
| 7 | H | 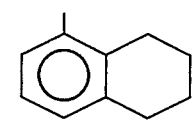 OCH₃, OCH₃, OCH₃ | A | 159~161 | $C_{14}H_{18}N_2O_5$ | 57.14 (56.99) | 6.16 (6.30) | 9.52 (9.47) |
| 8 | H | 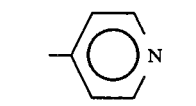 | A | 89.5~90.5 | $C_{15}H_{18}N_2O_2$ | 69.48 (69.75) | 7.08 (7.02) | 10.79 (10.84) |
| 9 | H | 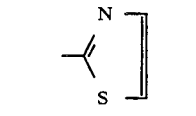 | A | 136~137 | $C_{10}H_{11}N_3O_2$ | 58.53 (58.43) | 5.40 (5.38) | 20.48 (20.46) |
| 10 | H | 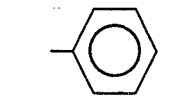 | A | 172~173 | $C_8H_9N_3O_2S$ | 45.49 (45.30) | 4.29 (4.36) | 19.89 (19.84) |
| 11 | 4-OH | 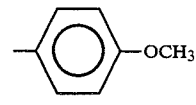 | A | 104~104.5 | $C_{11}H_{12}N_2O_3$ | 60.06 (59.99) | 5.57 (5.49) | 12.67 (12.72) |
| 12 | 4-OH | 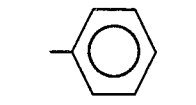 —OCH₃ | A | 116~118 | $C_{12}H_{14}N_2O_4$ | 57.88 (57.94) | 5.96 (5.64) | 11.09 (11.19) |
| 13 | 3-CH₃ | 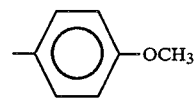 | A | 83~85 | $C_{12}H_{14}N_2O_2$ | 66.04 (66.05) | 6.47 (6.54) | 12.83 (12.84) |
| 14 | 3-CH₃ | 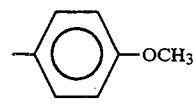 —OCH₃ | B | 71~72 | $C_{13}H_{16}N_2O_3$ | 62.83 (62.89) | 6.46 (6.50) | 11.26 (11.28) |
| 15 | 5-CH₃ | —OCH₃ | A | 50~50.5 | $C_{13}H_{16}N_2O_3$ | 62.77 (62.89) | 6.64 (6.50) | 11.24 (11.28) |

TABLE 1-continued

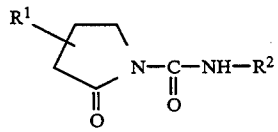

| Compd. No. | R¹ | R² | Process | m.p. (°C.) | Formula | Elementary analysis Calcd (Found) C | H | N |
|---|---|---|---|---|---|---|---|---|
| 16 | 5-CH$_2$OH | phenyl | A | 99~101 | C$_{12}$H$_{14}$N$_2$O$_3$ | 61.43 (61.06) | 6.02 (6.01) | 11.96 (11.91) |

TABLE 2

Antiamnesia effect
[increase ratio (%) of the step-through latency]
Dosage (mg/kg)

| Compd. No. | 300 | 100 | 30 | 10 |
|---|---|---|---|---|
| ① | +230 | +367 | +623 | +360 |
| ② | +507 | +623 | +557 | +346 |
| ⑤ | +79 | +213 | +598 | +119 |
| ⑥ | +596 | +568 | +138 | |
| ⑦ | +345 | +209 | −10 | |
| ⑧ | +414 | +490 | +531 | +125 |
| ⑨ | +41 | +157 | +245 | −7 |
| ⑩ | +475 | +144 | +166 | |
| ⑪ | +518 | +198 | +346 | |
| ⑭ | +1 | +6 | +75 | |
| ⑮ | +672 | +148 | +25 | |
| ⑯ | +50 | +103 | +135 | |
| Aniracetam | +42 | +288 | +230 | |

TABLE 3

Antianoxia activity
[increase ratio (%) of the survival time]
Dosage (mg/kg)

| Compd. No. | 300 | 100 | 30 | Acute toxicity LD$_{50}$ (mg/kg) |
|---|---|---|---|---|
| ① | +39 | +15 | −15 | 5000< |
| ② | +27 | +5 | +11 | 5000< |
| ③ | +46 | +15 | +11 | 2000< |
| ⑤ | +9 | +22 | −4 | <5000 |
| ⑥ | +14 | −4 | 0 | 5000< |
| ⑦ | +66 | +11 | +4 | 5000 |
| ⑧ | +20 | +25 | +30 | 5000< |
| ⑨ | +16 | +12 | +13 | <5000 |
| ⑩ | +35 | −1 | −4 | 5000 |
| ⑪ | +96 | +62 | +11 | |
| ⑫ | +63 | +7 | +5 | |
| ⑬ | +37 | +87 | +9 | 2000< |
| ⑭ | +34 | +26 | +9 | 5000< |
| ⑮ | +11 | −1 | −3 | 5000< |
| ⑯ | +89 | +36 | +10 | 5000 |
| Aniracetam | +23 | +26 | +19 | (4052)* |

Research on Toxicity of Aniracetam-Acute Toxicity Test with Mice and Rats, Japanese Pharmacology & Therapeutics, 14, Suppl. 4, 673–689 (1986), Mariko Shimizu, Naoaki Uchiya, Akiko Inoue, Miyuki Nonaka, Yoshiharu Yokoyama and Keiji Udaka.

EFFECT OF THE INVENTION

The medicaments for treating senile dementia must have cerebral function improving activity to ameliorate memory and learning disturbances and activity to activate the metabolism of cerebral nerve cells or to protect these cells from injuries and attacks. It is further desired that the medicaments be diminished in side effects and of high safety since the patients are aged people. When fulfilling these requirements, the medicaments are useful for treating senile dementia.

Tables 2 and 3 reveal that the present compounds exhibit antiamnesia activity and antianoxia activity and further have two activities, i.e., activity to improve cerebral functions and activity to activate cerebral metabolism or protect anoxic brain damage. The acute toxicity test indicates that the present compounds are at least 5000 mg/kg in LD$_{50}$ and are lower than Aniracetam in toxicity.

To sum up, the present compounds have two pharmacological activities, i.e., cerebral function improving activity and cerebral metabolism activating or anoxic brain damage protecting activity, low toxicity and therefore usefulness and are effective for treating senile dementia.

We claim:

1. A carbamoyl compound of the formula:

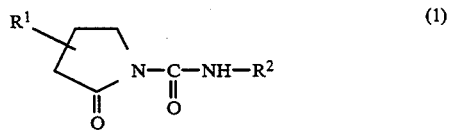

(1)

wherein R¹ is hydroxy or hydroxyl C$_1$–C$_5$ alkyl, and R² is phenyl, 5,6,7,8-tetrahydro-1-naphthyl, pyridyl, thiazolyl, or phenyl substituted by one or two methoxy or alkylamino groups selected from the group consisting of methylamino, dimethylamino, ethylamino, diethylamino, propylamino, and dipropylamino.

2. A carbamoyl compound of the formula:

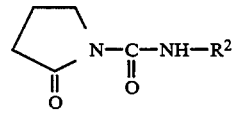

wherein R² is phenyl substituted by one or two methoxy or alkylamino groups selected from the group consisting of methylamino, dimethylamino, ethylamino, diethylamino, propylamino, and dipropylamino.

3. A carbamoyl compound of the formula

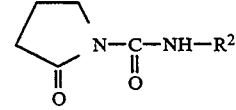

wherein R² is 5,6,7,8-tetrahydro-1-naphthyl, pyridyl, thiazolyl, p-methoxyphenyl, p-N,N-dimethylaminophenyl, or 3,4-dimethoxyphenyl.

4. The carbamoyl compound of claim 1 wherein $R_1$ is OH in the 4-position and $R^2$ is phenyl.

5. The carbamoyl compound of claim 1 wherein $R_1$ is hydroxymethyl in the 5-position and $R^2$ is phenyl.

6. The carbamoyl compound of claim 3 wherein $R^2$ is p-methoxyphenyl.

7. The carbamoyl compound of claim 3 wherein $R^2$ is p-N,N-dimethylaminophenyl.

8. The carbamoyl compound of claim 3 wherein $R^2$ is 3,4-dimethoxyphenyl.

9. The carbamoyl compound of claim 3 wherein $R^2$ is 5,6,7,8-tetrahydro-1-naphthyl.

10. The carbamoyl compound of claim 3 wherein $R^2$ is pyridyl.

11. The carbamoyl compound of claim 3 wherein $R^2$ is thiazolyl.

12. A composition for improving cerebral function and activating cerebral metabolism or protecting against anoxic brain damage, comprising an amount of a carbamoyl compound of claim 1 effective to cause such effects, in combination with a suitable pharmaceutical carrier.

13. A composition for improving cerebral function and activating cerebral metabolism or protecting against anoxic brain damage, comprising an amount of a carbamoyl compound of claim 3 effective to cause such effects, in combination with a suitable pharmaceutical carrier.

* * * * *